(12) United States Patent
Fallin et al.

(10) Patent No.: US 8,048,120 B1
(45) Date of Patent: Nov. 1, 2011

(54) SYSTEM AND METHOD FOR SEGMENTALLY MODULAR SPINAL PLATING

(75) Inventors: Thomas Wade Fallin, Hyde Park, UT (US); Daniel F. Justin, Logan, UT (US)

(73) Assignee: Medicine Lodge, Inc., Logan, UT (US)

( * ) Notice: Subject to any disclaimer, the term of this patent is extended or adjusted under 35 U.S.C. 154(b) by 470 days.

(21) Appl. No.: 11/809,602

(22) Filed: May 31, 2007

Related U.S. Application Data

(60) Provisional application No. 60/803,594, filed on May 31, 2006.

(51) Int. Cl.
*A61B 17/70* (2006.01)

(52) U.S. Cl. .......................... 606/249; 606/246; 606/248

(58) Field of Classification Search .................. 606/246, 606/247, 248, 249, 71, 70, 250, 278, 86 A; 623/17.16, 17.15, 17.11
See application file for complete search history.

(56) References Cited

U.S. PATENT DOCUMENTS

| | | | |
|---|---|---|---|
| 3,648,691 A | 3/1972 | Lumb et al. | |
| 5,496,318 A * | 3/1996 | Howland et al. | 606/249 |
| 5,645,599 A * | 7/1997 | Samani | 623/17.16 |
| 6,126,689 A * | 10/2000 | Brett | 623/17.16 |
| 6,331,179 B1 | 12/2001 | Freid et al. | 606/279 |
| 6,626,944 B1 * | 9/2003 | Taylor | 623/17.16 |
| 6,652,527 B2 * | 11/2003 | Zucherman et al. | 606/249 |
| 6,695,842 B2 * | 2/2004 | Zucherman et al. | 606/249 |
| 6,932,820 B2 | 8/2005 | Osman | |
| 6,946,000 B2 * | 9/2005 | Senegas et al. | 623/17.11 |
| 7,101,375 B2 * | 9/2006 | Zucherman et al. | 606/249 |
| 7,335,203 B2 * | 2/2008 | Winslow et al. | 606/249 |
| 7,442,208 B2 * | 10/2008 | Mathieu et al. | 623/17.11 |
| 2003/0040746 A1 * | 2/2003 | Mitchell et al. | 606/61 |
| 2004/0167625 A1 * | 8/2004 | Beyar et al. | 623/11.11 |
| 2004/0249379 A1 | 12/2004 | Winslow et al. | |
| 2005/0102028 A1 * | 5/2005 | Arnin et al. | 623/17.13 |
| 2005/0203512 A1 * | 9/2005 | Hawkins et al. | 606/61 |
| 2006/0015181 A1 | 1/2006 | Elberg | |
| 2006/0058790 A1 | 3/2006 | Carl et al. | |
| 2006/0085070 A1 * | 4/2006 | Kim | 623/17.11 |
| 2006/0247640 A1 * | 11/2006 | Blackwell et al. | 606/71 |
| 2007/0149972 A1 * | 6/2007 | Nakajima et al. | 606/61 |
| 2007/0270840 A1 * | 11/2007 | Chin et al. | 606/61 |
| 2008/0033552 A1 * | 2/2008 | Lee et al. | 623/17.11 |

FOREIGN PATENT DOCUMENTS

WO WO03007829 1/2003

* cited by examiner

*Primary Examiner* — Eduardo C Robert
*Assistant Examiner* — Nicholas Plionis
(74) *Attorney, Agent, or Firm* — Peter K. Johnson; James Larson; Barbara Daniels

(57) ABSTRACT

A modular implant for stabilizing the relative motion of spinal vertebrae comprises at least two pairs of plates which connect to two adjacent spinous processes, a spacer configured to be positioned between the spinous processes, and a fastener which pivotably connects to the plates and the spacer. The spacer is interchangeable and may comprise a variety of materials, each providing a different level of elasticity to the spinous processes. Relative motion between vertebrae can also be controlled by varying the surface configuration of the plates and by varying threading of the fastener. Several implants may be linked to provide stabilization across multiple vertebral levels, and the relative motion provided at each vertebral level may differ. A method for revising the implant is provided which comprises accessing the implant and replacing the spacer.

22 Claims, 10 Drawing Sheets

SYSTEM AND METHOD FOR SEGMENTALLY MODULAR SPINAL PLATING

CROSS-REFERENCE TO RELATED APPLICATIONS

This application claims the benefit of the following, which is incorporated herein by reference:

Pending prior U.S. Provisional Patent Application No. 60/803,594, filed May 31, 2006 by T. Wade Fallin et al., which carries Applicants' docket no. MLI-57 PROV, and is entitled SYSTEM AND METHOD FOR SEGMENTALLY MODULAR SPINAL PLATING.

BACKGROUND OF THE INVENTION

1. The Field of the Invention

The present invention relates generally to spinal orthopedics, and more specifically, to posterior implants designed to dynamically stabilize or immobilize one or more spinal motion segments.

2. The Relevant Technology

Orthopedic medicine provides a wide array of implants that can be attached to bone to alleviate various pathologies. Due to the degeneration of spinal tissues, it can be desirable to dynamically stabilize, or even immobilize, adjacent vertebral levels. Unfortunately, currently available implants are often usable only to treat a very narrow range of pathologies. Many such devices are also bulky, difficult to implant, or difficult to revise. There is a need in the art for posterior spinal implants capable of providing dynamic stabilization at a desired level of stiffness so that a variety of pathologies can be treated via first implantation or revision.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for stabilizing the relative motion of spinal vertebrae. Those of skill in the art will recognize that the following description is merely illustrative of the principles of the invention, which may be applied in various ways to provide many different alternative embodiments.

Figure 1:
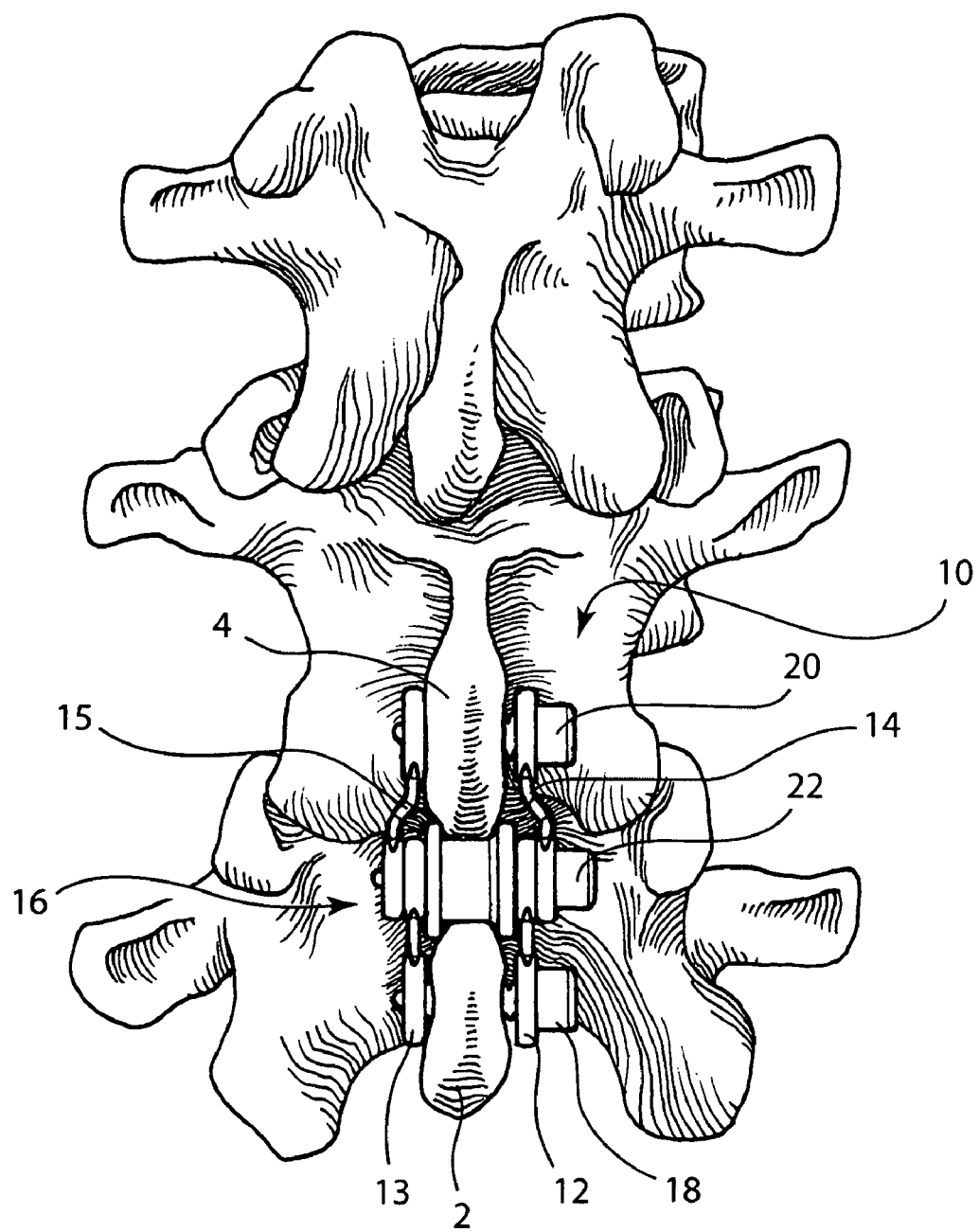
FIG. 1 is a posterior view of a segmentally modular spinal plating system fixed to a portion of the spine.

Referring to FIG. 1, a posterior view illustrates a segmentally modular spinal plating system 10 affixed to a portion of the lumbar spine. The system 10 comprises a non-threaded straight plate 12, a singly-threaded straight plate 13, a non-threaded jogged plate 14, a doubly-threaded jogged plate 15, and a spacer assembly 16. The straight plates 12, 13 lie on both lateral sides of the spinous process 2 of the lower vertebra, and are connected by a fastener 18 which passes through the non-threaded straight plate 12, through the spinous process 2, and through the singly-threaded straight plate 13. The jogged plates 14, 15 lie on both lateral sides of the spinous process 4 of the adjacent vertebra above and are connected by a fastener 20 which passes through the non-threaded jogged plate 14, through the spinous process 4 and through the doubly-threaded jogged plate 15. Between the two spinous processes 2, 4, the spacer assembly 16 is connected to both of the straight plates 12, 13 and both of the jogged plates 14, 15 by a fastener 22. The fastener 22 lies transverse to the spinal column on an axis about which the plates can pivot; this axis extends along the medial/lateral direction (i.e., left-to-right when viewing FIG. 1).

Figure 2:
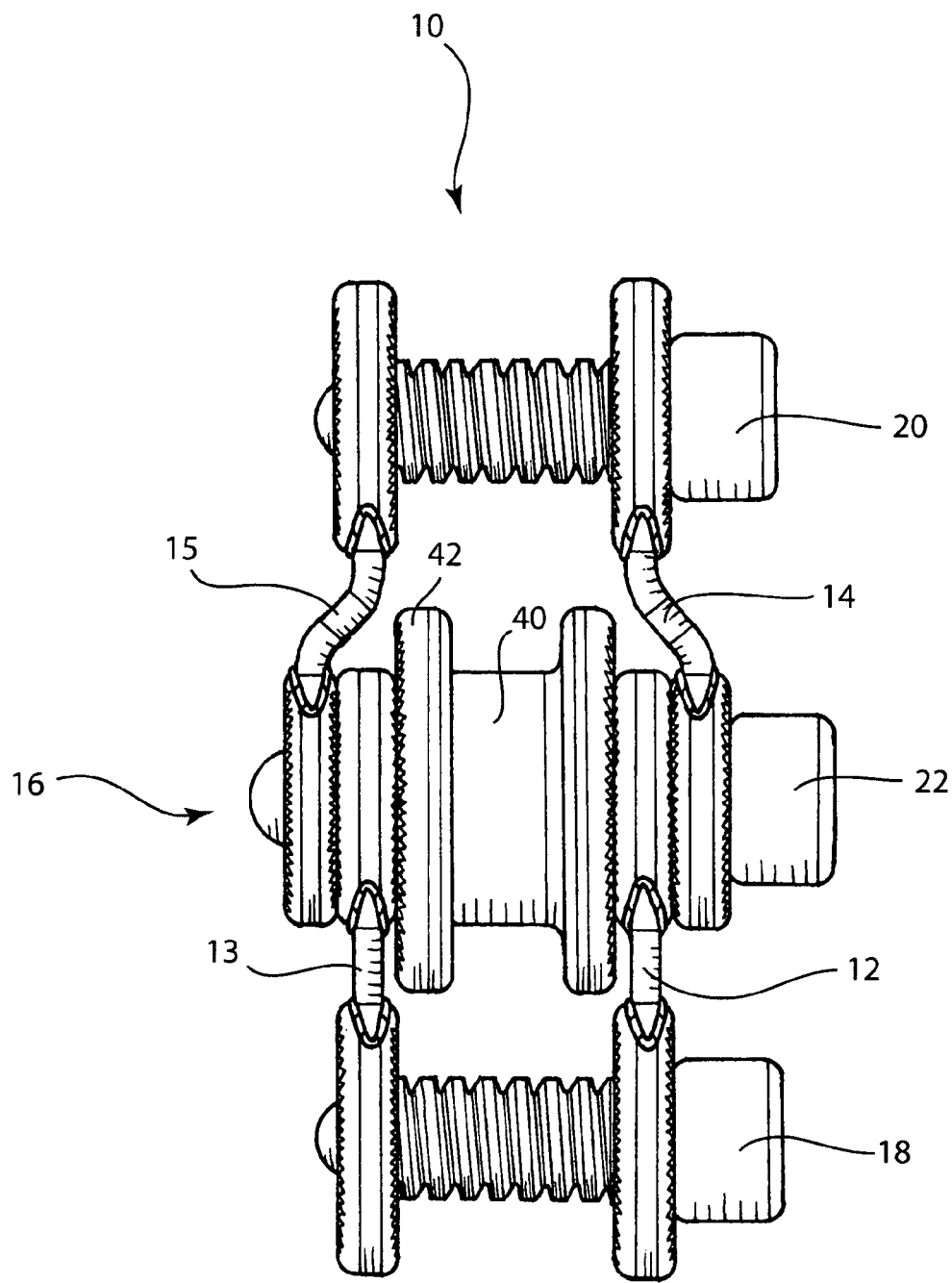
FIG. 2 is a posterior view of the segmentally modular spinal plating system of FIG. 1, which includes a spacer assembly, a pair of straight plates, a pair of jogged plates, and three fasteners.

Referring to FIG. 2, an enlarged posterior view illustrates the segmentally modular spinal plating system 10 in more detail. The two straight plates 12, 13 are secured by a fastener 18. The two jogged plates 14, 15 are secured by a fastener 20. "Jogged plates" refers to plates which are not planar between two ends, but are non-planar or bent between two ends. The straight plates 12, 13 and the jogged plates 14, 15 are linked together by the spacer assembly 16. In the embodiment depicted in FIG. 2, the spacer assembly 16 includes a spacing member 40 and a rim cap 42. The spacer assembly 16 is threaded on the fastener 22. In alternative embodiments, the spacer assembly 16 is a one-piece unitary construct. In the embodiment depicted, the fasteners 18, 20, 22 are threaded bolts. In alternative embodiments, the fasteners 18, 20, 22 need not be threaded bolts but could be non-threaded bolts, bolts with nuts, screws, pins, or rivets, among others.

Figure 3:
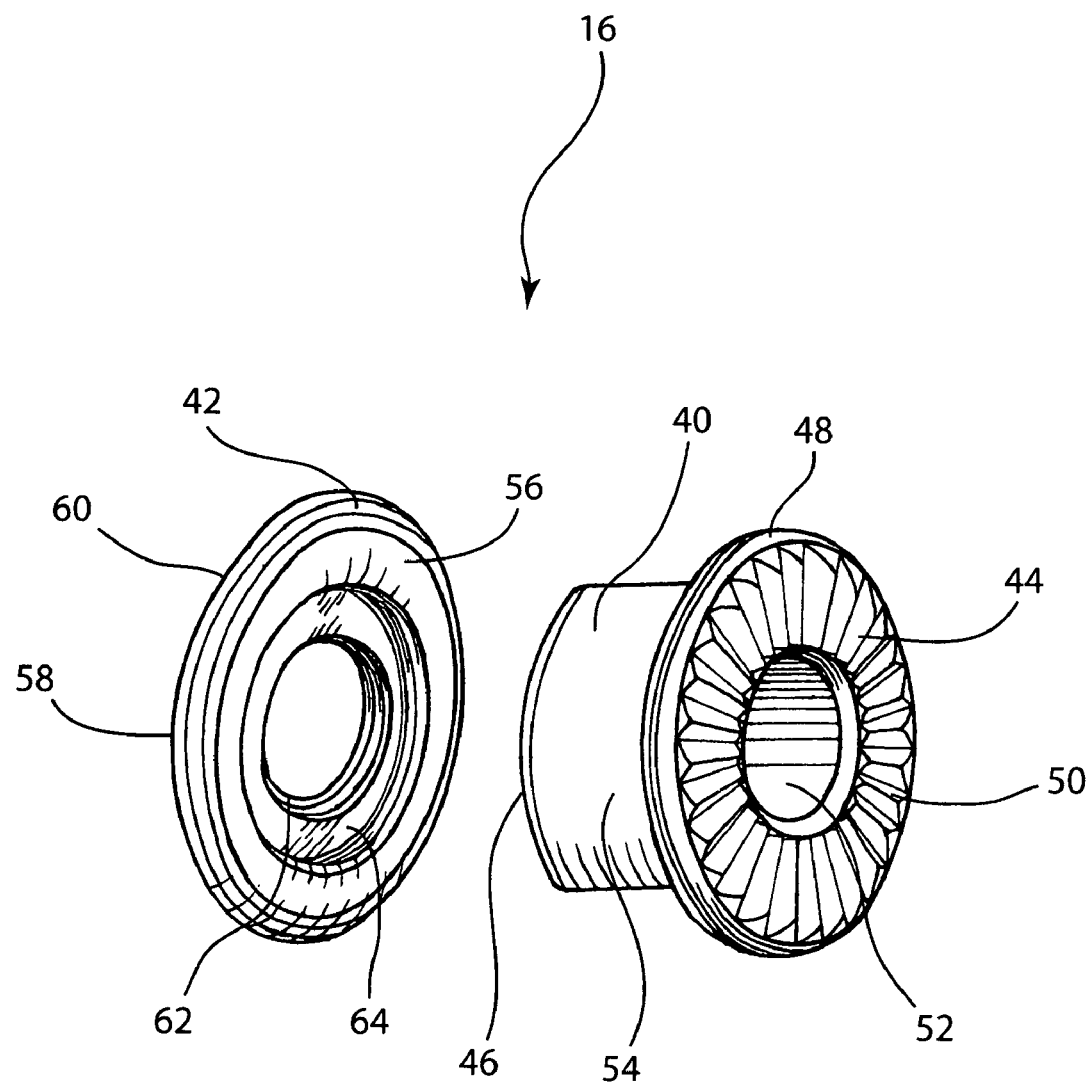
FIG. 3 is a perspective view of the spacer assembly of FIG. 2.

FIG. 3 illustrates the spacer assembly 16 in an enlarged perspective view. The spacing member 40 is generally tubular in form; however, the shape of the spacing member 40 is such that it best conforms to the morphology of the area on the spinous processes 2,4 which it contacts and can be other non-circular, more organic, bone conforming shapes. The spacing member 40 has an outer end 44 and an inner end 46. The outer end 44 is wider in diameter than the rest of the spacing member 40, and forms a flange-like shape along a rim 48. A radial spline 50 occupies an outer interface surface 49 of the rim 48. A bore 52 extends through the longitudinal center of the spacing member 40. The outer cylindrical wall of the spacing member is a bearing surface 54.

The rim cap 42 is generally flat and circular, and has an inner side 56 and an outer interface side 58. Depressed into the inner side 56 is a concavity 64. A diameter of the concavity 64 is sized to hold the inner end 46 of the spacing member 40. A radial spline 60 (not visible in FIG. 3) occupies an outer interface surface 59 of the outer side 58. A bore 62 runs through the center of the rim cap 42.

When implanted as part of the segmentally modular spinal plating device 10, the spacing member 40 (particularly the bearing surface 54) and the rim cap 42 come in contact with the sides and outer edge of the spinous processes 2, 4 as seen in FIG. 1. To serve different stabilization purposes, the spacing member 40 and rim cap 42 may be composed of a variety of materials. If dynamic stabilization is desired, the spacing member 40 and rim cap 42 can be composed of a semi-rigid, elastically compliant biocompatible polymer such as polyurethane or the spacing member 40 may be designed with spring elements (not shown) that allow flexibility and compressibility of the spacer assembly 16 when it is loaded by the spinous processes 2 and 4. If stabilization is desired, the spacing member 40 and rim cap 42 can be composed of a substantially rigid biocompatible materials including metals such as titanium, cobalt chromium alloys, stainless steel alloys or the like or other substantially rigid materials such as PEEK, Ultra High Molecular weight polyethylene (UHMWPE), Delrin, ceramics, or other biocompatible structural engineering polymers or ceramics. If fusion is desired, the spacing member 40 and rim cap 42 may be composed of natural or synthetic bone material. Finally, if completely dynamic movement is desired, the device 10 may be implanted without a spacer 40 and rim cap 42, and with a non-threaded rod replacing the fastener 22.

Figure 4:
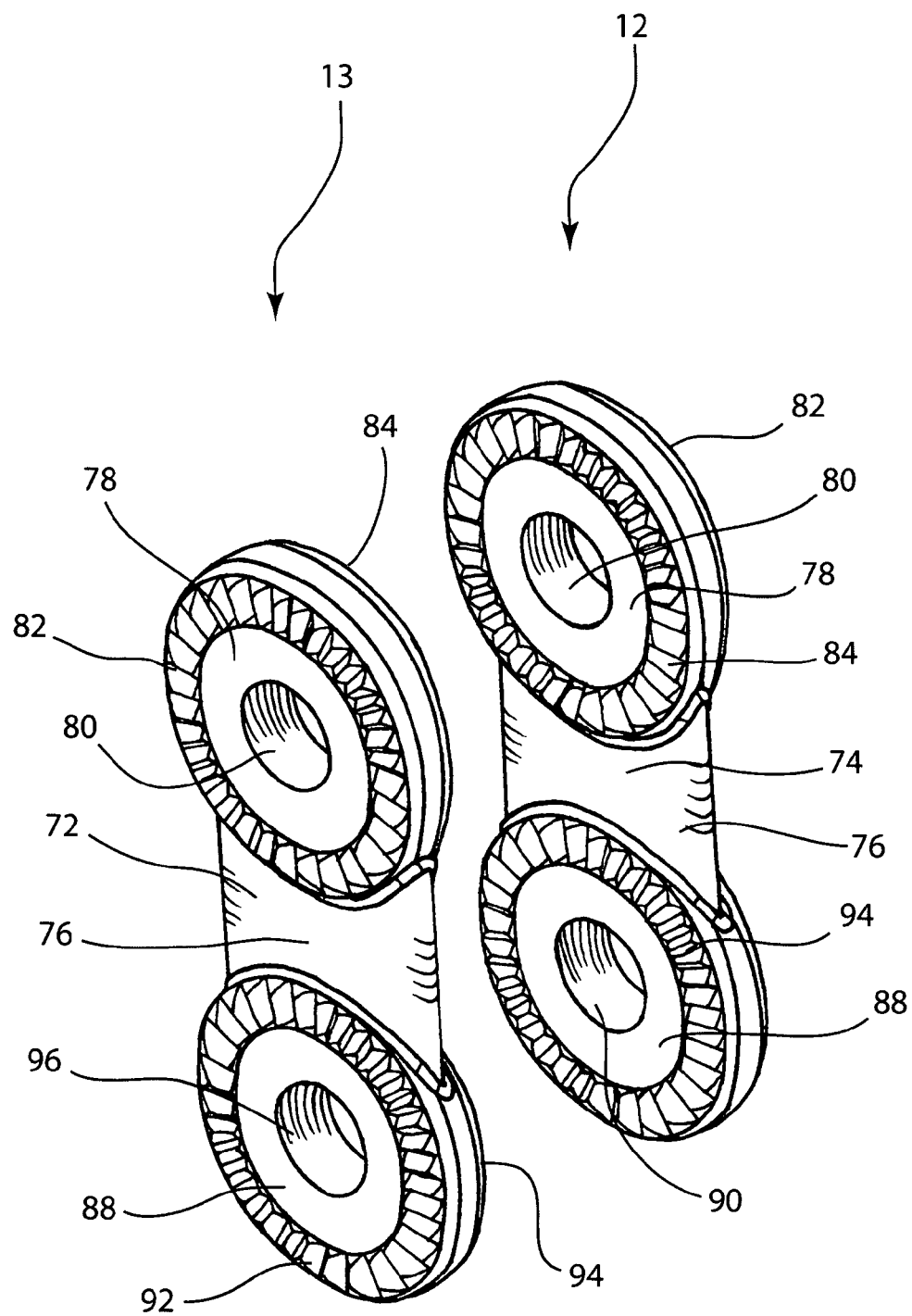
FIG. 4 is a perspective view of the straight plates of FIG. 2.

Referring to FIG. 4, an enlarged view shows the non-threaded straight plate 12 and the singly-threaded straight plate 13. The two straight plates 12, 13 are substantially identical to each other in shape and are symmetrical from side to side. The only difference between the straight plates 12, 13 is whether or not the bores in the plates are threaded. Each straight plate 12, 13 has a substantially planar, elongated elliptical shape with an outer facing side 72 and an inner facing side 74. The center of each straight plate 12, 13 is a planar member 76, which is terminated at one longitudinal end by a first annulus 78. A non-threaded bore 80 perforates the first annulus 78. An outer facing radial spline 82 is an outer interface surface 79 of the first annulus 78, and an inner facing radial spline 84 is on an inner interface surface 81 of the first annulus 78.

The opposite longitudinal end of the planar member 76 is terminated by a second annulus 88. On the non-threaded straight plate 12, a non-threaded bore 90 perforates the second annulus 88. On the singly-threaded straight plate 13, a threaded bore 96 perforates the second annulus 88. An outer facing radial spline 92 is on an outer interface surface 89 of the second annulus 88, and an inner facing radial spline 94 is an inner interface surface 91 of the second annulus 88. Because the non-threaded straight plate 12 has two non-threaded bores 80, 90, and is otherwise symmetrical, it may be turned side to side or end to end prior to assembly in the device 10. However, the singly-threaded straight plate 13 has one non-threaded bore 80 and one threaded bore 96. Thus, it may be turned side to side but not end to end to be properly assembled in the device 10.

Figure 5:
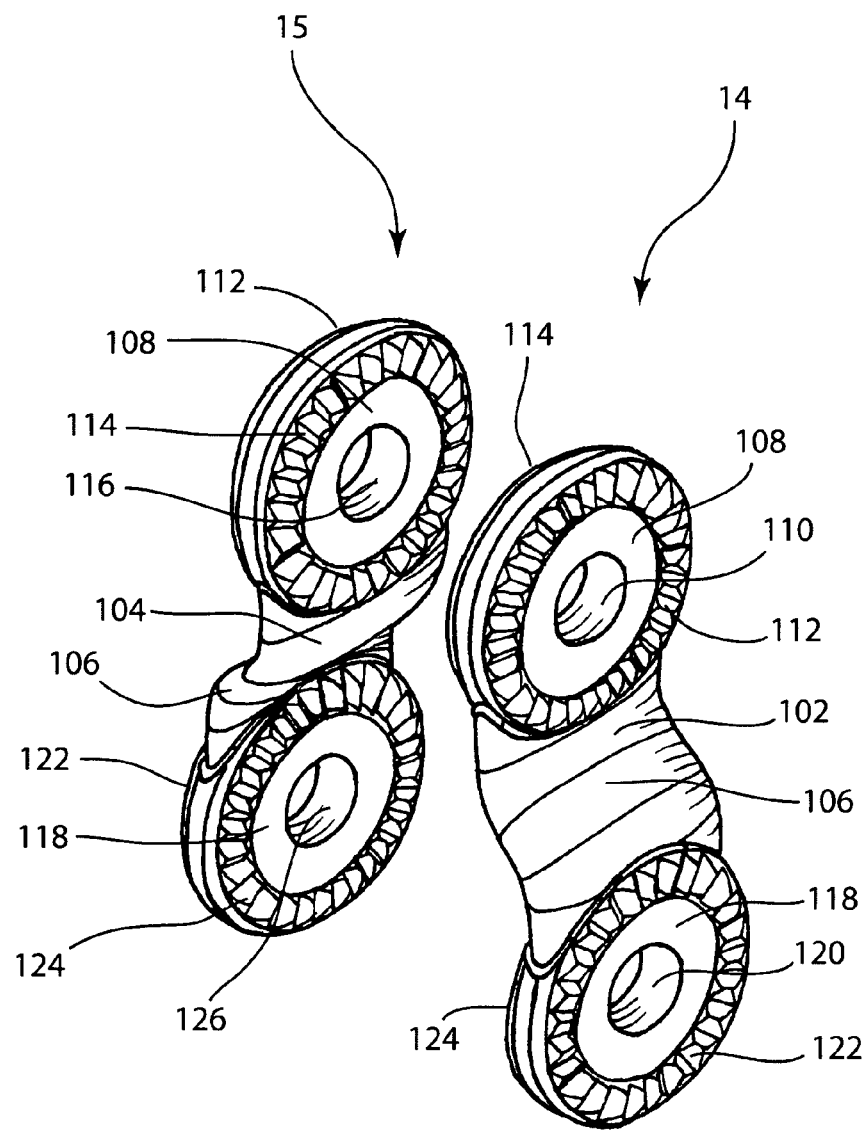
FIG. 5 is a perspective view of the jogged plates of FIG. 2.

FIG. 5 displays the two jogged plates 14, 15. As with the straight plates 12, 13, the jogged plates 14, 15 are identical to each other except for the threading of the bores. Each jogged plate 14, 15 has an outer facing side 102 and an inner facing side 104. A central jogged member 106 terminates at one longitudinal end at a first annulus 108. On the non-threaded jogged plate 14, a non-threaded bore 110 perforates the first annulus 108. On the doubly-threaded jogged plate 15, a threaded bore 116 perforates the first annulus 108. On both jogged plates 14, 15 an outer facing radial spline 112 is on an outer interface surface 109 of the first annulus 108, and an inner facing radial spline 114 is on an inner interface surface 111 of the first annulus 108.

The opposite longitudinal end of the jogged member 106 is terminated at a second annulus 118. On the non-threaded jogged plate 14, a non-threaded bore 120 perforates the second annulus 118. On the doubly-threaded jogged plate 15, a threaded bore 126 perforates the second annulus 118. On each jogged plate 14, 15, an outer facing radial spline 122 is on an outer interface surface 119 of the second annulus 118, and an inner facing radial spline 124 is on an inner interface surface 121 of the second annulus 118. Because of the non-planar configuration of the jogged plates, the jogged plates 14, 15 cannot be turned side to side or end to end but must be specifically oriented to be properly assembled in the system 10.

Figure 6:
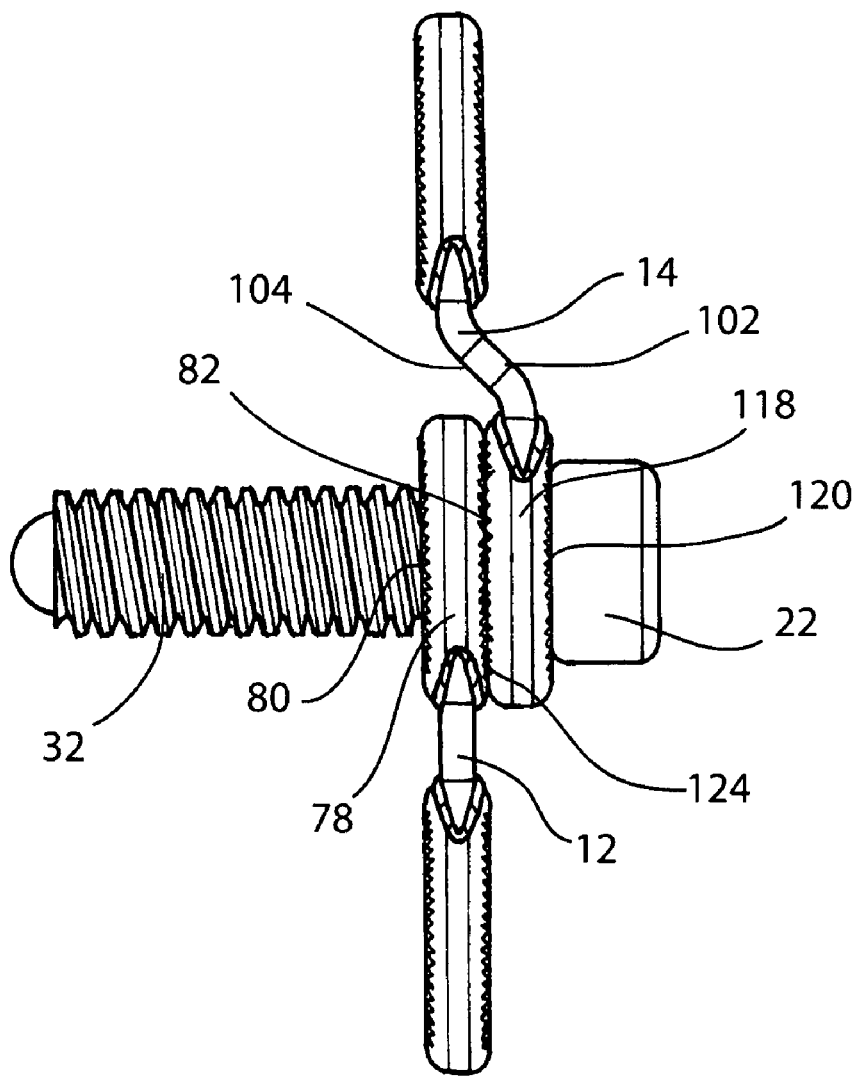
FIG. 6 is a posterior view of a partial assembly of one straight plate of FIG. 4 joined by a fastener to one jogged plate of FIG. 5.

FIGS. 6 through 9 show the steps in assembly of the device 10. FIG. 6 depicts the fastener 22 with the non-threaded straight plate 12 and the non-threaded jogged plate 14. During assembly, first the non-threaded jogged plate 14 is placed onto the fastener 22. A threaded shaft 32 of the fastener 22 is placed through the bore 120 of the second annulus 118, from the outer facing side 102 to the inner facing side 104. The non-threaded jogged plate 14 is slid along the shaft 32 until the second annulus 118 contacts a fastener head 34.

Following placement of the non-threaded jogged plate 14 as described above, the non-threaded straight plate 12 is put onto the fastener 22. The bore 80 on the first annulus 78 is slid along the threaded shaft 32, until the first annulus 78 contacts the non-threaded jogged plate 14. At this point, the inner radial spline 124 of the non-threaded jogged plate 14 engages with the outer radial spline 82 of the non-threaded straight plate 12, causing the plates 12, 14 to releasably lock into place relative to one another. The interaction of the radial splines 124, 82 allows for very precise adjustment to obtain the desired length of the device 10. During the implantation process, the angle at which the plates 12, 14 engage may be adjusted by pulling the plates apart, rotating one plate or another around the shaft 32 until the desired position of the plates about the axis is found, then pushing the plates 12, 14 back together so that the radial splines 82, 124 engage. Because the bores 80, 120 of the plates 12, 14 are not threaded, they can freely rotate around the shaft 32 until locked into place by meshing the splines. Adjusting the angle of the plates 12, 14 about the axis adjusts the length of the device 10. The axis is defined by interaction between the bores of the plates and the outer surface of the fastener shaft 32.

Figure 7:
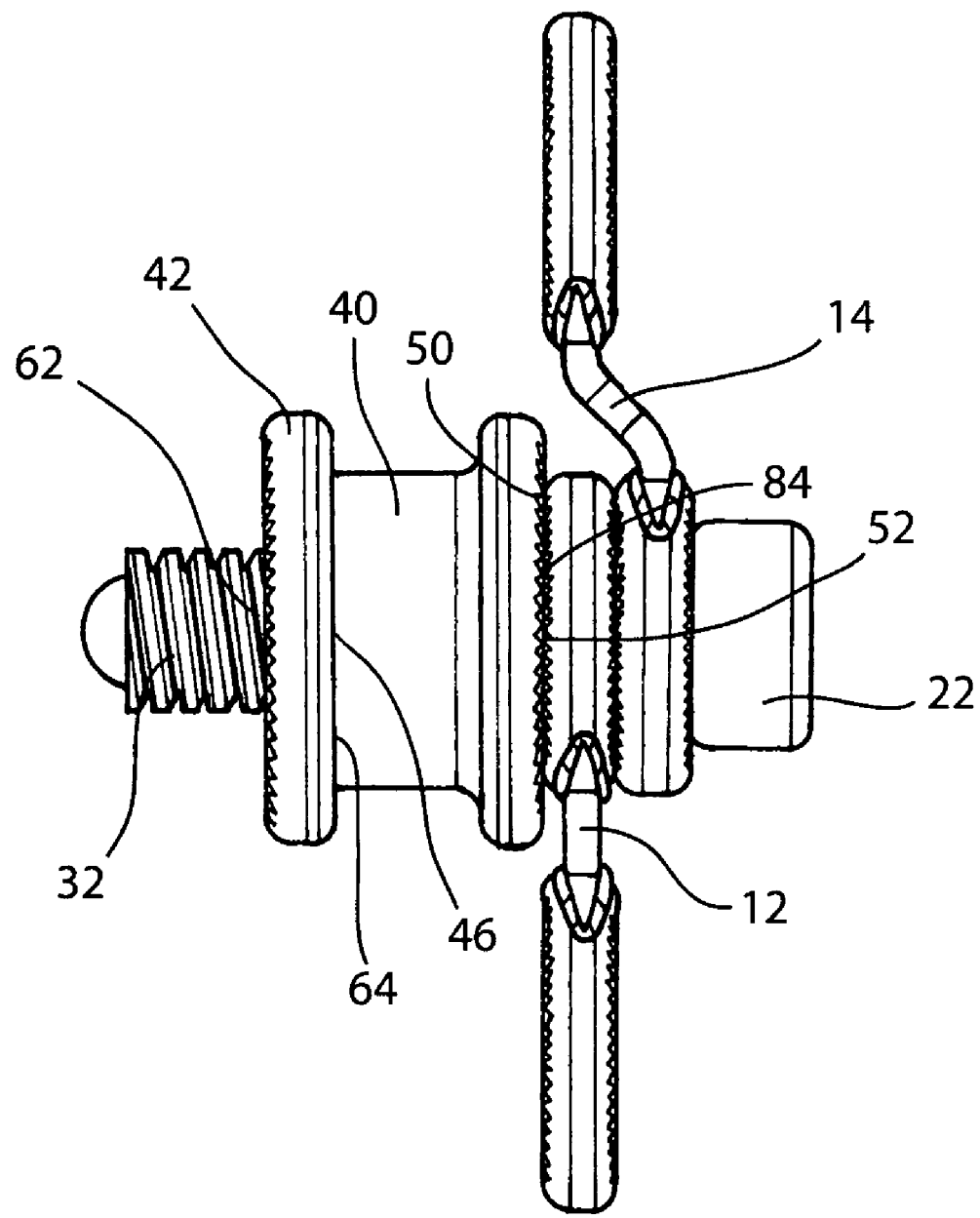
FIG. 7 is a posterior view of the partial assembly of FIG. 6, joined to the spacer assembly of FIG. 3.

FIG. 7 illustrates the addition of the spacer assembly 16 to the partial assembly depicted in FIG. 6. The bore 52 of the spacer member 40 is slid onto the threaded shaft 32 of the fastener 22. The spacer member 40 is slid onto the fastener 22 until the outer radial spline 50 of the spacer member 40 engages with the inner radial spline 84 of the non-threaded straight plate 12. The rim cap 42 is then slid onto the fastener 22. The bore 62 of the rim cap 42 is slid onto the threaded shaft 32 of the fastener 22, until the concavity 64 fits over the inner end 46 of the spacer member 40. Alternatively, the spacer member 40 and the rim cap 42 may first be press fit or threaded together, with the inner end 46 fitting into the concavity 64, and then slid as a single piece onto the fastener 22.

Figure 8:
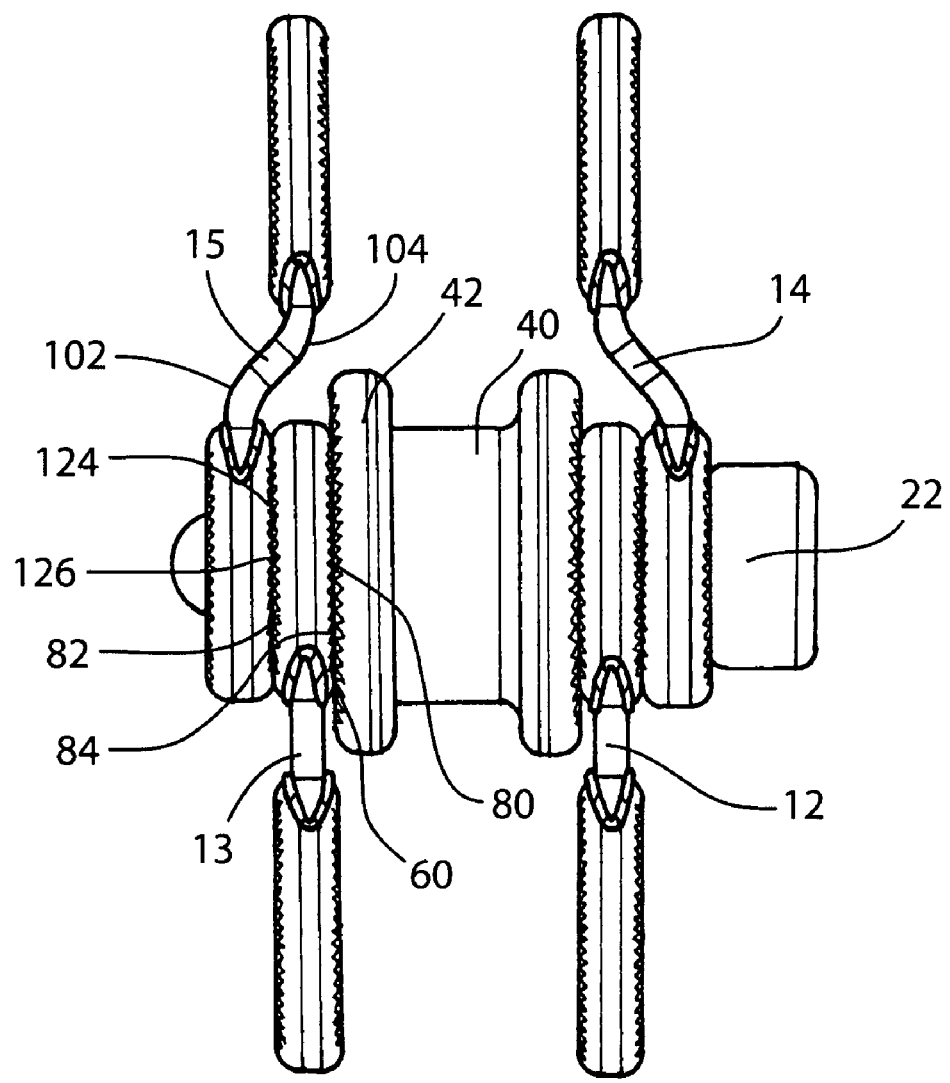
FIG. 8 is a posterior view of the partial assembly of FIG. 7, joined to an additional straight plate and an additional jogged plate.

Referring to FIG. 8, the singly-threaded straight plate 13 and the doubly-threaded jogged plate 15 are shown as added to the partial assembly depicted in FIG. 7. The non-threaded bore 80 of the first annulus 78 on the singly-threaded straight plate 13 is slid onto the threaded shaft 32 (not visible) of the fastener 22. When the first annulus 78 contacts the rim cap 42, the inner radial spline 84 of the singly-threaded straight plate 13 engages with the outer radial spline 60 on the rim cap 42. In the manner described above, during implantation the singly-threaded straight plate 13 may be rotated around the threaded shaft 32 until the desired position about the axis is achieved, before the meshing of the splines 60, 84 releasably locks the singly-threaded plate 13 into place.

The doubly-threaded jogged plate 15 is the last plate to be added to the assembly. The threaded bore 126 on its second annulus 118 is screwed onto the threaded shaft 32, until the inner radial spline 124 engages with the outer radial spline 82 on the singly-threaded straight plate 13. As with plates 12 and 14, plates 13 and 15 may be adjusted about axis until the desired angle and length for the device 10 is found.

Figure 9:
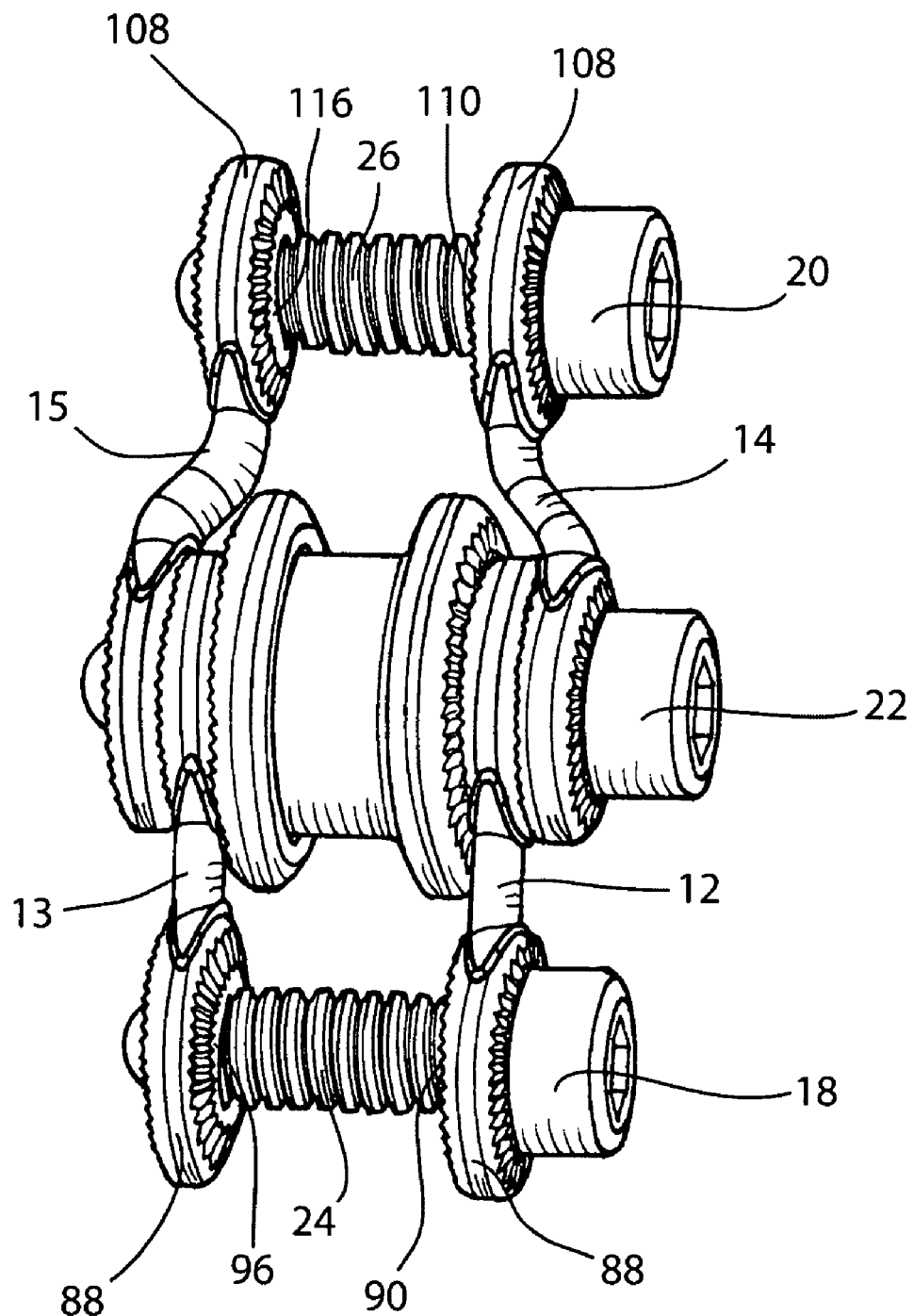
FIG. 9 is a posterior perspective view of the segmentally modular spinal plating system of FIG. 1.

FIG. 9 depicts the system 10 as fully assembled, with the fasteners 18 and 20 in place. Before the fasteners 18, 20 are added, the partially assembled system 10 is placed on the spine so that the spacing member 40 is between the spinous processes 2, 4 of the vertebrae. The two first annuli 108 of the jogged plates 14, 15 extend in a cephalad direction on either side of the upper spinous process 4. The two second annuli 88 of the straight plates 12, 13 extend in a caudal direction on either side of the lower spinous process 2. The threaded shaft 24 of the fastener 18 passes through the non-threaded bore 90 of the non-threaded straight plate 12, through the spinous process 2 of the lower vertebra, then screws into the threaded bore 96 of the singly-threaded straight plate 13. The engagement of the threads on the threaded shaft 24 with the threads in the threaded bore 96 tightens the fastener 18 in place. Similarly, the threaded shaft 26 of the fastener 20 passes through the non-threaded bore 110 of the non-threaded jogged plate 14, through the spinous process 4 of the upper vertebra, then screws into the threaded bore 116 of the doubly-threaded jogged plate 15. The engagement of threads on the threaded shaft 26 with the threads in the threaded bore 116 tightens the fastener 20 into place. In the embodiment depicted, fasteners 18 and 20 pass through the spinous processes 2 and 4 to fasten the plates to the spinous processes. However, in other embodiments, other means of attachment may be used to fasten the plates to the spinous processes, such as bands, clamps, cables, wire, and sutures, among others.

Figure 10:
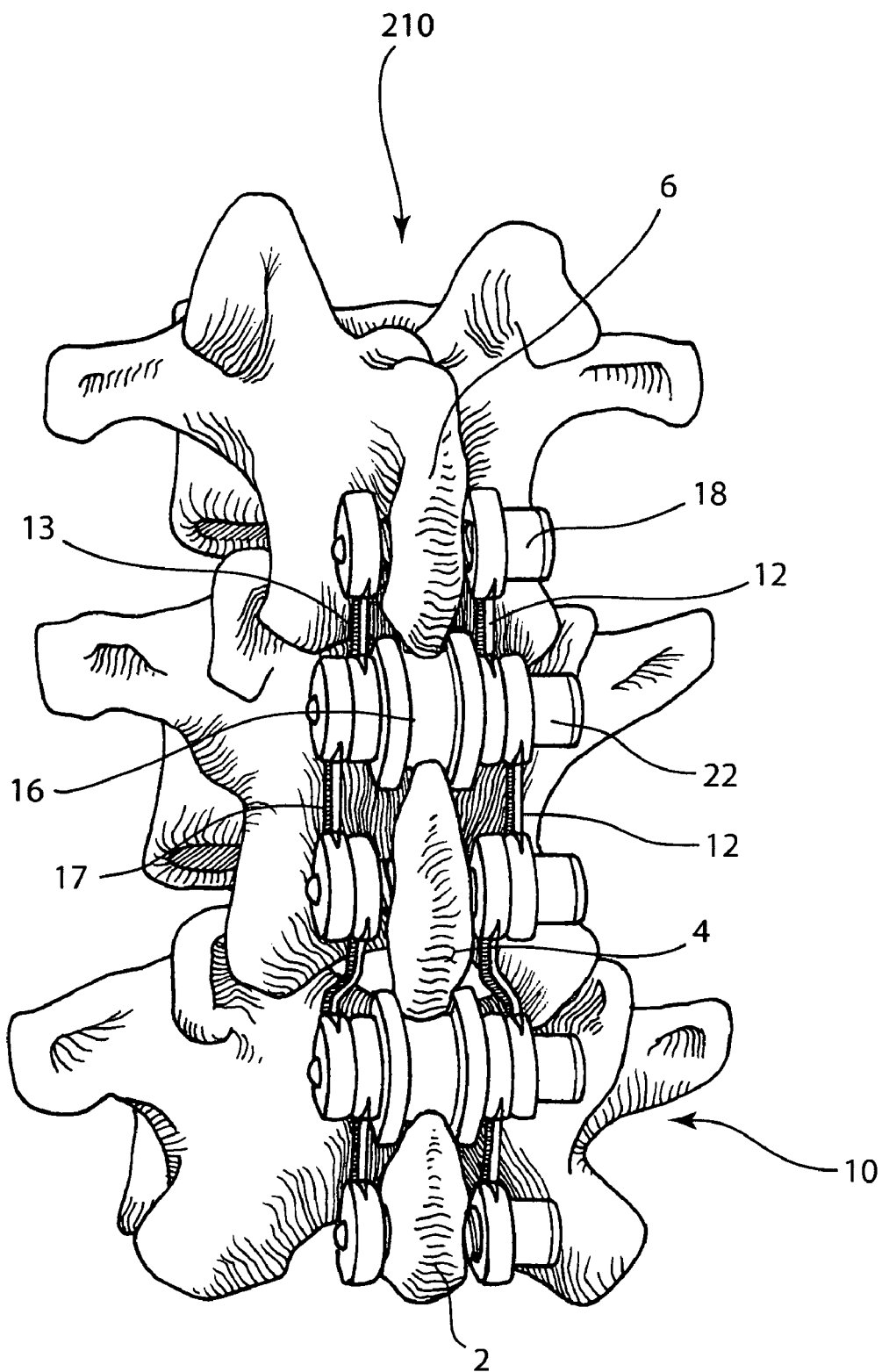
FIG. 10 is a posterior perspective view of a two-level segmentally modular spinal plating system fixed to a portion of the spine.

FIG. 10 illustrates a two-level segmentally modular spinal plating system 210 fixed in place in a portion of the spine. The system 210 comprises a single level system 10, plus two additional non-threaded straight plates 12, an additional singly-threaded straight plate 13, a doubly-threaded straight plate 17, an additional spacer assembly 16, and two additional fasteners. A non-threaded straight plate 12 and the doubly-threaded straight plate 17 are added to the upper level of the single level system 10, and connect the single level system 10 to an additional fastener 22. The fastener 22 retains the non-threaded straight plate 12, a second non-threaded straight plate 12, a spacer assembly 16, a singly-threaded straight plate 13, and the doubly-threaded straight plate 17. The spacer assembly 16 fits between the spinous processes 4 and 6. A final fastener 18 retains one non-threaded straight plate 12 and the singly-threaded straight plate 13. When a two level system 210 is utilized, the two spacer assemblies 16 may be composed of like material to provide similar stabilization between all involved vertebrae, or the two spacer assemblies 16 may be of different materials to provide different types of stabilization between the different vertebrae. The two level system 210 enables stabilization between three vertebrae; additional levels may be added if desired, again with interchangeable spacer assemblies 16.

The embodiments depicted in FIGS. 1 through 10 utilize a threaded bolt for each of the fasteners 18, 20, 22, and plates 12, 13, 14, 15 with bores that are threaded or not threaded. An alternative embodiment could have bolt fasteners that are shallowly threaded along most of the shaft, and deeply threaded at the end of the shaft. In this alternative, all the bores of the plate could be threaded, but only the plates that connect at the end of the shaft (the outermost plates) would threadably engage the shaft (where the shaft is deeply threaded) and tighten onto the fastener. In yet another alternative, the plates need not be threaded at all but a threaded nut could be added on the end of the threaded fastener shaft to tighten all the components together.

Another alternative embodiment (not shown) does not have radial splines on the outer or inner interface surfaces of the plates or other means of regulating movement between the plates. This allows for dynamic movement between the plates since the interface between the plates is not restricted by any mechanism that prevent rotation or sliding between the plates. Plates according to this alternative embodiment, when used in conjunction with a more elastically compliant spacer, allow for more dynamic movement between vertebrae.

Another embodiment (not shown) permits dynamic movement between the plates, as in the embodiment of the preceding paragraph, and also provides resilient force, for example, via the addition of springs, to stabilize such dynamic movement. For example, torsional springs (not shown) may be registered on the plates 12, 14, on the plates 13, 15, or at the junctions between both pairs of plates 12, 14, 13, 15. In the alternative, damping force may be applied to the motion between the plates 12, 14, 13, 15, for example, through the use of a frictional yet movable interface (not shown) such as frictional coatings on the various interface surfaces of the plates 12, 14, 13, 15, or a sealed chamber containing a viscous fluid and a damper that moves through the fluid in response to relative rotation between the plates 12, 14, 13, 15 (not shown). These are merely examples; those of skill in the art will recognize that many other mechanisms may be used to provide resilient force, damping force, or some combination of the two between the plates 12, 14, 13, 15 to control relative motion between the spinous processes 2, 4.

The present invention may be embodied in other specific forms without departing from its spirit or essential characteristics. It is appreciated that various features of the above-described examples can be mixed and matched to form a variety of other alternatives, each of which may have different plates, spacer assembly or threading system according to the invention. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An implantable modular device for stabilizing relative motion of spinal vertebrae, comprising:
 a first pair of plates attachable to a first spinous process;
 a second pair of plates attachable to a second spinous process;
 a first spacing member positionable to fit between the first and second spinous processes to provide a selected level of stiffness between the spinous processes, the first spacing member comprising a first bearing surface and a second bearing surface orthogonal to the first bearing surface, the first bearing surface positionable to contact an inferior surface of the first spinous process and a superior surface of the second spinous process, the second bearing surface shaped as a continuous annulus, the second bearing surface positionable to directly contact a lateral surface of the first spinous process and an ipsilateral surface of the second spinous process; and a fastener joining the first spacing member and the first and second pairs of plates, the fastener comprising a head and a shaft, the shaft having a first end and a second end and a longitudinal axis extending therebetween, the shaft first end passing freely through the first pair of plates and the spacing member and then directly engaging an outermost one of the second pair of plates to join the first pair of plates, the second pair of plates and the spacing member together along the longitudinal axis of the fastener shaft between the head and the shaft first end, wherein the first and second pairs of plates are rotatably attachable together at any of a variety of relative orientations in response to securement of the fastener to the first and second pairs of plates to permit further relative rotation between the pairs of plates, thereby permitting dynamic relative motion between the first and second spinous processes.

2. The device of claim 1, wherein the first spacing member is interchangeable with a different spacing member to permit variation in the stiffness between the spinous processes, wherein each spacing member comprises a material chosen from the group consisting of biocompatible polymers, metals, natural tissues, and synthetic tissues.

3. The device of claim 1, further comprising:
a third pair of plates attachable to the second spinous process via an attachment mechanism that also attaches the second pair of plates to the second spinous process;
a fourth pair of plates attachable to a third spinous process;
a second spacing member configured to fit between the second and third spinous processes to provide a selected level of stiffness between the spinous processes; and
at least one additional fastener joining the second spacing member to the third and fourth pairs of plates.

4. The device of claim 1, wherein the first and second pairs of plates are further configured to be rigidly attached together at any of the variety of relative orientations in response to securement of the first fastener to the first and second pairs of plates to substantially prevent further relative rotation between the pairs of plates, thereby keeping the first and second spinous processes at a substantially fixed relative displacement.

5. The device of claim 1, wherein the first pair of plates are substantially planar.

6. The device of claim 5, wherein the second pair of plates are non-planar.

7. The device of claim 1, wherein the fastener shaft is threaded and the outermost one of the second pair of plates comprises a threaded bore, the threaded fastener shaft threadibly engaging the threaded bore to axially draw the first pair of plates, the second pair of plates and the spacer together along the longitudinal axis of the fastener shaft.

8. An implantable modular device for stabilizing relative motion of spinal vertebrae, comprising:
a first pair of plates attachable to a first spinous process immediately adjacent a second spinous process, the first pair of plates comprising a first plate and a second plate, the first plate having a first bore extending transversely therethrough and a second bore extending transversely therethrough, the first bore spaced apart from, and parallel to, the second bore, the second plate having a third bore extending transversely therethrough and a fourth bore extending transversely therethrough, the third bore spaced apart from, and parallel to, the fourth bore;

a second pair of plates attachable to the second spinous process, the second pair of plates comprising a third plate and a fourth plate, the third plate having a fifth bore extending transversely therethrough and a sixth bore extending transversely therethrough, the fifth bore spaced apart from the sixth bore, the fourth plate having a seventh bore extending transversely therethrough and an eighth bore extending transversely therethrough, the seventh bore spaced apart from the eighth bore; and a first fastener having a shaft with a longitudinal axis, the shaft extending freely through the first bore, the third bore, and the sixth bore to join to the first and second pairs of plates, the first fastener directly engaged with the eighth bore to axially draw the first and second pairs of plates together along the shaft axis, wherein the first and second pairs of plates are configured to be rigidly attached together at any of a variety of relative orientations in response to securement of the first fastener to the first and second pairs of plates to substantially prevent further relative rotation between the pairs of plates, thereby keeping the first and second spinous process at a substantially fixed relative displacement.

9. The device of claim 8, further comprising a second fastener comprising a shaft, the shaft configured to pass through the second bore and the fourth bore, parallel to the first fastener, to join to the first and second plates, wherein the shaft comprises a threaded portion and the fourth bore comprises threads, wherein the threaded portion of the shaft is directly engageable with the fourth bore threads to axially draw the first and second plates together.

10. The device of claim 9, further comprising:
a third fastener, the third fastener configured to pass through the fifth bore and the seventh bore, wherein the seventh bore comprises threads, and wherein the third fastener is engageable with the threaded seventh bore to axially draw the third and fourth plates together.

11. The device of claim 8, further comprising: a first spacing member configured to fit between the first and second spinous processes to provide a selected level of stiffness between the spinous processes, the first spacing member positioned between the first and second plates with the first bore, the first spacing member and the third bore axially aligned, wherein the first fastener passes through the spacing member.

12. The device of claim 8, wherein each of the first, third and sixth bores is free of threading, allowing the fastener to extend freely through the first, third and sixth bores.

13. The device of claim 12,
wherein the eighth bore is threaded; and
wherein the first fastener shaft is threaded and directly engageable with the threaded eighth bore to axially draw the first and second pairs of plates together.

14. The device of claim 8, wherein at least one of the first and second pairs of plates is substantially non-planar.

15. The device of claim 8, wherein at least one of the first and second plates further comprises a first interface surface comprising a plurality of ridges, and at least one of the third and fourth plates further comprises a second interface surface comprising a plurality of ridges, wherein the ridges of the first interface surface are directly engageable with the ridges of the second interface surface to lock the first and second pairs of plates together at any of the variety of relative orientations.

16. An implantable modular device for providing dynamic relative motion of spinal vertebrae, comprising:

a first pair of plates attachable to a first spinous process, the first pair of plates comprising a first plate and a second plate;

a second pair of plates attachable to a second spinous process, the second pair of plates comprising a third plate and a fourth plate;

a first spacing member comprising a first bearing surface, the first spacing member configured to fit between the first and second spinous processes to provide a selected level of stiffness between the spinous processes, and a fastener formed separately from the first spacing member, the fastener having a shaft and a fastener axis and extending through the first plate, the third plate, the spacing member, the fourth plate, and the second plate in sequence, the fastener shaft passing freely through the first plate, the third plate, the spacing member and the fourth plate, and directly engaging the second plate to urge the first and second pairs of plates into direct engagement with one another to permit relative rotation between the pairs of plates about the fastener axis while in direct engagement, thereby permitting dynamic relative motion between the first and second spinous processes, wherein the first spacing member further comprises a locking feature, wherein the locking feature is lockable with one of the first and second pairs of plates to lock the first spacing member to one of the first and second pairs of plates.

17. The device of claim 16, wherein at least one of the first and second plates further comprises a first interface surface, and at least one of the third and fourth plates further comprises a second interface surface, wherein the first interface surface is in slidable contact with the second interface surface when the first pair of plates is in direct engagement with the second pair of plates.

18. The device of claim 16, wherein the first bearing surface is configured to contact an inferior surface of the first spinous process and a superior surface of the second spinous process; and wherein the first spacing member further comprises a second bearing surface, the second bearing surface shaped as a continuous annulus, the second bearing surface configured to directly contact a lateral surface of the first spinous process and an ipsilateral surface of the second spinous process.

19. The device of claim 16, wherein the first spacing member is elastically compliant.

20. The device of claim 16, wherein the first spacing member is configured to provide resilient force to stabilize the dynamic relative motion.

21. The device of claim 16, wherein the locking feature is lockable with the third plate and the fourth plate at any of a variety of relative orientations.

22. The device of claim 16, wherein the first spacing member comprises a material chosen from the group consisting of biocompatible polymers, metals, natural tissues, and synthetic tissues.

* * * * *